United States Patent [19]

Clapp et al.

[11] Patent Number: 5,597,806
[45] Date of Patent: Jan. 28, 1997

[54] ANTIFUNGAL AGENTS

[75] Inventors: Wendy H. Clapp, New York, N.Y.; Guy H. Harris, Cranford, N.J.; Gerald F. Bills, Clark, N.J.; James E. Curotto, Morgan, N.J.; Anne W. Dombrowski, East Brunswick, N.J.; Sarah J. Driekorn, Scotch Plains, N.J.; Myra B. Kurtz, Martinsville, N.J.; Maria S. Meinz, Fair Haven, N.J.; Janet C. Onishi, Westfield, N.J.; Jon D. Polishook, Cranford, N.J.; Stanley L. Streicher, Verona, N.J.; John R. Thompson, Scotch Plains, N.J.; Marie Williams, Cranford, N.J.; Deborah L. Zink, Manalapan, N.J.

[73] Assignee: Merck & Co., Inc., Rahway, N.J.

[21] Appl. No.: 437,718

[22] Filed: May 9, 1995

[51] Int. Cl.$^6$ .............................. A61K 31/71; C07J 19/00
[52] U.S. Cl. .............................. 514/25; 435/78; 435/822; 536/5
[58] Field of Search .................................. 536/5; 514/25; 435/78, 822

[56] References Cited

U.S. PATENT DOCUMENTS 5,426,179 6/1995 Bertolini et al. .............................. 536/5
5,455,335 10/1995 Kahne et al. .............................. 536/5

FOREIGN PATENT DOCUMENTS 03119993 5/1991 Japan .

OTHER PUBLICATIONS

Gerald F. Bills et al., *Mycotaxon*, XLIII, pp. 453–460 (1992).
Gerald F. Bills et al., *Sydowia*, 44, pp. 1–12 (1992).
John E. Leet et et al., *Am. Soc. Pharm. 36th Annual Meeting* Jul. 23–27, 1995.

*Primary Examiner*—Elli Peselev
*Attorney, Agent, or Firm*—Elliott Korsen; Mark R. Daniel

[57] ABSTRACT

There are disclosed novel compounds having the formula

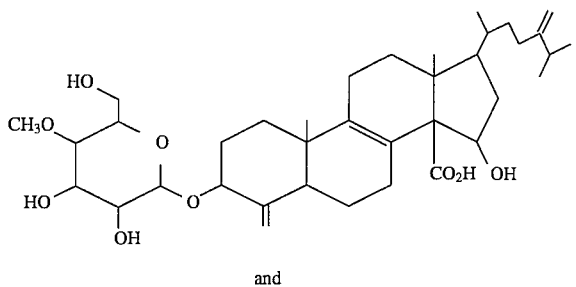

and

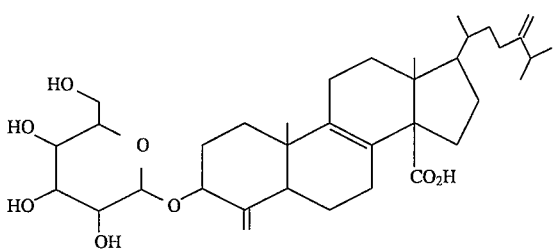

which exhibit antifungal activity.

7 Claims, 2 Drawing Sheets

ANTIFUNGAL AGENTS

BACKGROUND OF THE INVENTION

The present invention relates to novel antifungal compounds, compositions containing said compounds, processes for the production of said compounds and methods of using said compounds. Clinical treatment of human fungal infections has relied mainly on two classes of antifungal agents. These agents are amphotericin B, which is fungicidal and capable of curing fungal infections at the cost of severe side effects to the patient, and ketoconazole and other azole agents, which exhibit fewer side effects but which are only fungistatic.

The present compounds and compositions are fungicidal and exhibit broad spectrum antifungal activity against human fungal pathogens.

SUMMARY OF THE INVENTION

The present invention is directed to compounds (I) and (II) of the formula:

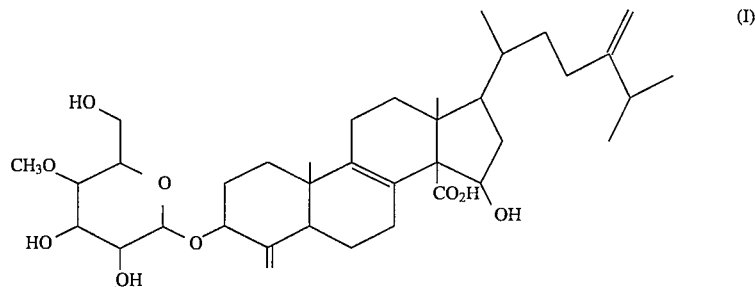

(I)

and

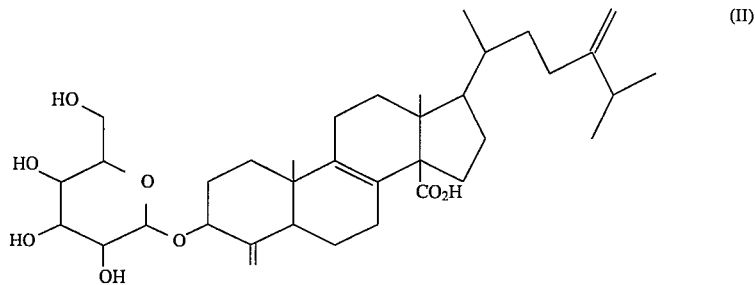

(II)

The compounds have antimicrobial and fungicidal properties and may be useful for controlling systemic and superficial fungal infections in humans with fewer side effects than standard antifungal agents such as amphotericin B or ketoconazole. In particular, the compounds are significantly less lytic to red blood cells than amphotericin B.

The compounds are obtained by cultivation of the endophytic fungus, *Mycoleptodiscus atromaculans*, MF 5928 (ATCC Designation 74336) in the Microbial Resources Culture Collection of Merck & Co., Inc., Rahway, N.J.

BRIEF DESCRIPTION OF THE DRAWINGS

FIG. I is a proton nuclear magnetic resonance spectrum for Compound I. The peak shown at approximately 3.30 ppm represents the solvent, $CD_3OD$. FIG. II is a proton nuclear magnetic resonance spectrum for Compound II.

DETAILED DESCRIPTION OF THE INVENTION

Figure 1:
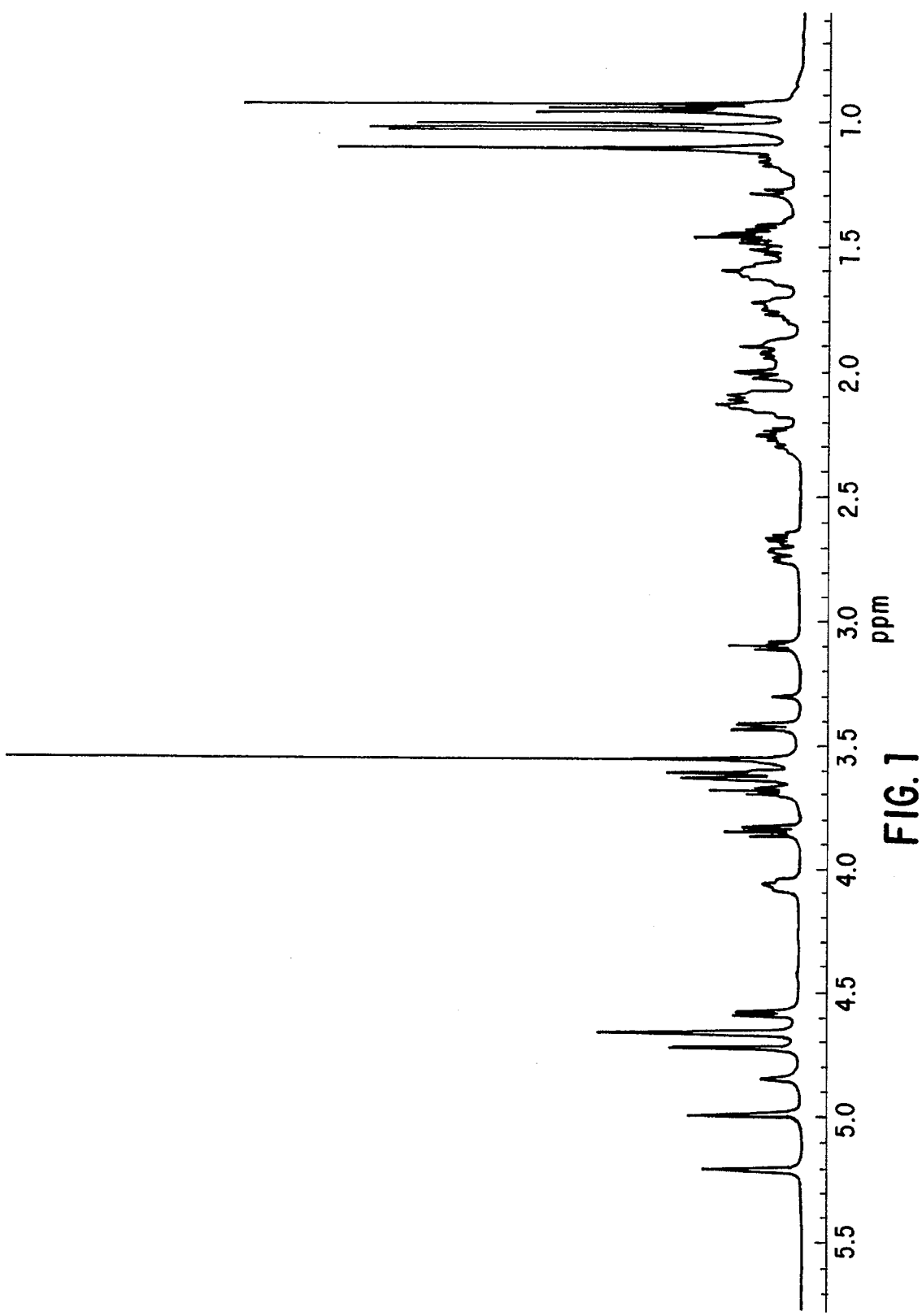
Figure 2:
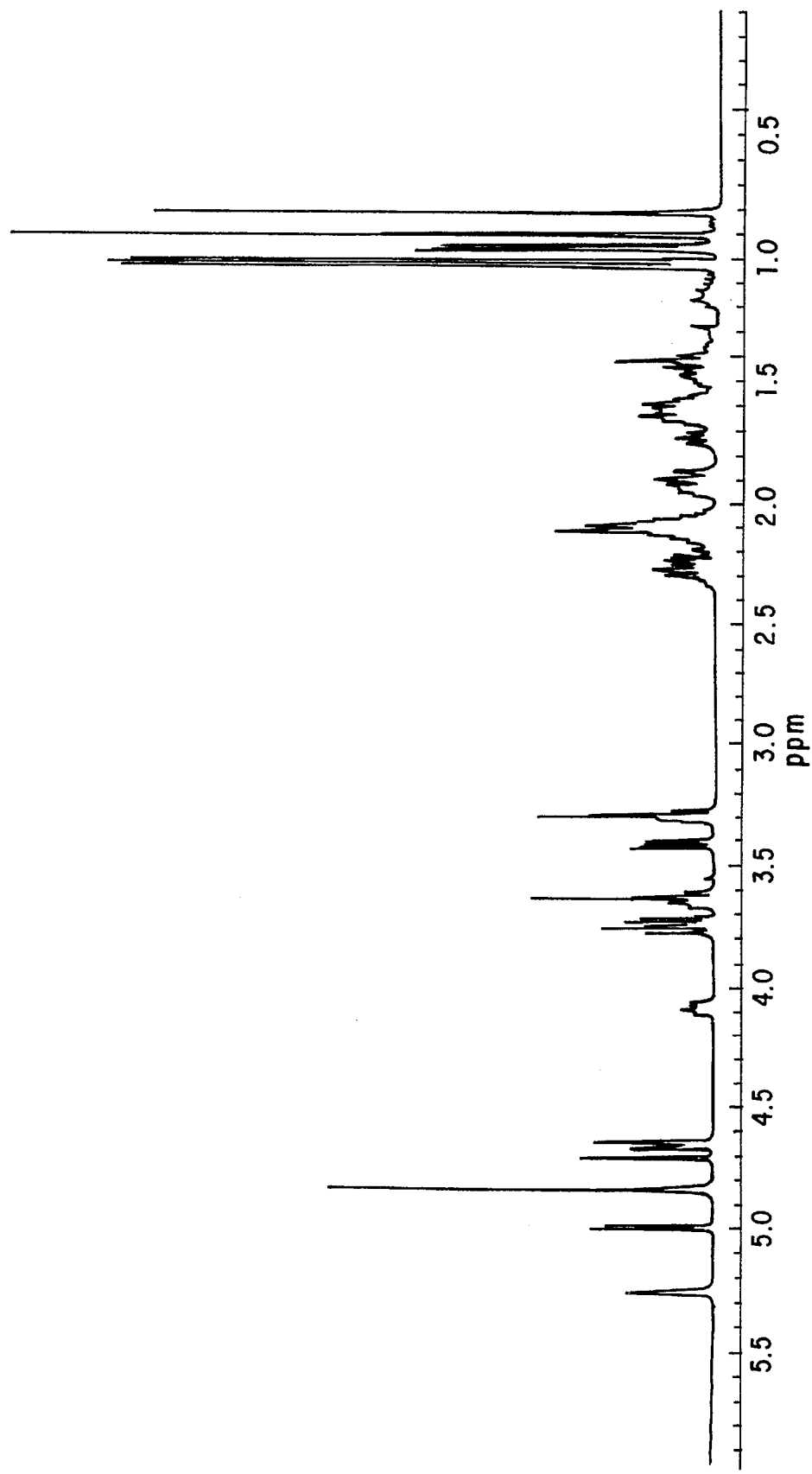

The compounds are off-white and characterized by the following spectral properties:

Compound I

ULTRAVIOLET SPECTRAL DATA $\lambda_{max}$(MeOH):203 nm; 235 nm (sh)

Optical Rotation Data

The optical rotation of Compound I was recorded on a Perkin Elmer 241 polarimeter at 20° C. in MeOH.

$[\alpha]_D^{20}$=+33°(c 0.64)

INFRARED SPECTRAL DATA

The infrared spectrum was recorded as a thin film on ZnSe using a Perkin Elmer Model 1750 FT infrared spectrometer. 2930, 1699, 1147, 1087, 887 cm$^{-1}$

Mass Spectral Data

Mass spectra were recorded on a Jeol SX-102A (electron impact, EI, 90 eV) mass spectrometer. Exact mass measurements were performed at high resolution (HR-EI) using perfluorokerosene (PFK) as internal standard. Trimethylsilyl derivatives were prepared with a 1:1 mixture of BSTFA-pyridine at room temperature. The APCI (atmospheric pressure chemical ionization) spectra were recorded on a Finnigan TSQ700.

The molecular ion was observed by APCI at m/z 647 (646+H). There was observed a neutral loss of water from the molecular ion at m/z 629. The molecular ion was also observed as the tetra-TMS derivative at m/z 934 by EI. In the underivatized EI-MS spectra, there was observed M-$CO_2$ at m/z 602.

HREI-MS

Found for $C_{36}H_{58}O_7$ 602.4193

Calculated for $C_{37}H_{58}O_9$-$CO_2$ 602.4182

NMR Spectral Data

$^{13}$C NMR Spectra

The $^{13}$C NMR spectrum of Compound I was recorded in CD$_3$OD at 125 MHz on a Varian Unity 500 spectrometer at 25° C. Chemical shifts are given in ppm relative to tetramethylsilane (TMS) at zero ppm and referenced to the internal solvent peak at 49.0 ppm.

$^{13}$C NMR Shifts for Compound I (4.5 mg in 0.14 mL CD$_3$OD, 25° C.): δ18.9, 19.2, 19.3, 22.1, 22.3, 22.5, 24.6, 27.2, 29.5, 31.9, 34.0, 34.9, 36.0, 36.3, 36.7, 40.7, 44.6, 47.6, 47.9, 51.9, 60.8, 62.2, 67.8, 73.06, 73.14, 73.7, 75.2, 76.7, 81.2, 96.8, 104.5, 106.9, 128.7, 141.1, 151.6, 157.7, 179.0.

$^1$H NMR Spectrum

The $^1$H NMR spectrum of Compound I is seen in FIG. I. The $^1$H NMR spectrum of Compound I (4.5 mg) was recorded in CD$_3$OD (0.14 mL) at 500 MHz on a Varian Unity 500 spectrometer at 25° C. Chemical shifts are given in ppm relative to tetramethylsilane (TMS) at zero ppm and referenced to the internal solvent peak at 3.30 ppm.

Compound II

Ultraviolet Spectral Data $\lambda_{max}$(MeOH): 203 nm; 235 nm (sh)

Optical Rotation Data

The optical rotation of Compound II was recorded on a Perkin Elmer 241 polarimeter at 20° C. in MeOH.
$[\alpha]_D^{20} = +102°(c0.50)$

Infrared Spectral Data

The infrared spectrum was recorded as a thin film on ZnSe using a Perkin Elmer Model 1750 FT infrared spectrometer. 2960, 2937, 1688, 1377, 1153, 1108, 1051, 1031, 888 cm$^{-1}$

Mass Spectral Data

Mass spectra were recorded on a Jeol SX-102A (electron impact, EI, 90eV) mass spectrometer. Exact mass measurements were preformed at high resolution (HR-EI) using perfluorokerosene (PFK) as internal standard. The ESI (electrospray ionization) spectra were recorded on a Finnigan TSQ700.

The molecular ion was observed by ESI at m/z 617 (616 +H). There was observed a loss of carboxylate from the molecular ion at m/z 571. In the underivatized EI-MS spectra, there was observed M-CO$_2$ at m/z 572.
HREI-MS Found for C$^{35}$H$^{56}$O$_6$ 572.4083
Calculated for C$_{36}$H$_{56}$O$_8$—CO$_2$ 572.4077

NMR Spectral Data $^{13}$C NMR Spectra
The $^{13}$C NMR spectrum of Compound II was recorded in CD$_3$OD at 125 MHz on a Varian Unity 500 spectrometer at 25 ° C. Chemical shifts are given in ppm relative to tetramethylsilane (TMS) at zero ppm and referenced to the internal solvent peak at 49.0 ppm.

$^{13}$C NMR Shifts for Compound I (5.9 mg in 0.13 mL CD$_3$OD, 25 ° C.): δα18.3, 18.6, 19.1, 22.0, 22.3, 22.5, 24.4, 27.7, 29.0, 29.4, 30.2, 32.1, 32.8, 34.9, 36.0, 36.1, 37.1, 40.4, 47.8, 48.1, 52.0, 62.7, 63.8, 71.9, 73.6, 74.0, 75.2, 76.7, 96.9, 104.6, 106.9, 129.1, 140.0, 151.3, 157.7, 180.1

$^1$H NMR Spectrum

The H NMR spectrum of Compound II is seen in FIG. II. The $^1$H NMR spectrum of Compound II (8.9 mg) was recorded in CD$_3$OD (0.7 mL) at 400 MHz on a Varian Unity 400 spectrometer at 25° C. Chemical shifts are given in ppm relative to tetramethylsilane (TMS) at zero ppm and referenced to the internal solvent peak at 3.30 ppm.

The compounds of this invention have antimicrobial properties and are especially useful as an antifungal agent against both filamentous fungi and yeasts. They are useful against organisms causing systemic human pathogenic mycotic infections such as *Candida albicans, Candida tropicalis, Cryptococcus neofromans, Aspergillus fumigatus, Candida pseudotropicalis, Saccharomyces cerevisiae, Aspergillus flavus* et al. They are also useful against organisms causing superficial fungal infections such as *Trichophyton sp.* and *Candida sp.* These properties may be effectively utilized by administering compositions containing an antifungal amount of Compound I or II to an area, object or subject, on or in which fungi are to be controlled. Thus, compositions containing an antifungally effective amount of Compound I or II and their use for the control of fungi are aspects of the present invention. An especially preferred aspect of the present invention are compositions in a pharmaceutically acceptable carder and their use for the control of mycotic infections by administering a therapeutically effective amount of one or both of the compounds.

The compounds of the present invention are fungal metabolites isolated using bioassay guided extraction and chromatography from liquid fermentations of wild strains of the endophytic fungus, *Mycoleptodiscus atromaculans*, e.g. MF5928 (ATCC Designation 74336) which was recovered from living leaves of *Chamaecyparis thyoides* (Atlantic white cedar) collected in Ocean Co., N.J. MF 5928 has been deposited under the Budapest Treaty in the culture collection of the American Type Culture Collection on Apr. 20, 1995 at 12301 Parklawn Drive, Rockville, Md. 20852 and assigned accession number ATCC Designation 74336.

*Mycoleptodiscus atromaculans* is one the most characteristic and abundant fungi associated with living foliage of *C. thyoides* (Bills, G. F. & J. D. Polishook. 1992a. Recovery of endophytic fungi from *Chamaecyparis thyoides*. Sydowia 44: 1–12; Bills, G. F. & J. D. Polishook. 1992b. A new species of Mycoleptodiscus from living foliage of *Chamaecyparis thyoides* Mycotaxon 43:453–460). For this reason, one skilled in mycology can predictably obtain *M. atromaculans* from leaves of *C. thyoides* by using the isolation protocols described in Bills & Polishook 1992a. The distincitive morphology of this fungus (illustrated in Bills & Polishook, 1992b) allows it to be easily separated and distinguished from other endophytic fungi co-inhabiting the same leaf tissues.

In the following description, cultures were grown on oatmeal agar(OA), cornmeal agar (CM), and malt-yeast extract (YM) agar (all Difco), at 50% relative humidity, 25° C., under continuous fluorescent light for 14 days. (Capitalized color names are from R. Ridgway (1912), Color Standards and Nomenclature, Washington, D.C). Conidial measurements include the length of terminal appendages.

In agar culture, colonies of the fungus exhibit the following morphology:

Colonies on oatmeal agar (Difco) 60–65 mm diam., slightly raised, radially plicate, zonate, with some medium buckling and cracking beneath center of colony, aerial mycelium moderately abundant to sparse at the margin, floccose to minutely hispid, with black sporodochia scattered beneath aerial mycelium over inner third of colony, margin entire, white to pale or medium gray, Pale Drab Gray, Pale Smoke Gray.

Colonies on CM agar (Difco), 55–60 mm diam., plane, zonate, submerged with scant aerial mycelium,, margin even to wavy, at first hyaline but soon developing the same colors as above, often with irregular lines or rows of black sporodochial masses radiating outward from inoculation point.

Colonies on YM agar (Difco) 50–55 mm diam., slightly raised, radially plicate or not, zonate to concentrically wrinkled, aerial mycelium floccose to minutely hispid, without sporodochia, white to hyaline at the margin, margin even to slightly wavy, reverse zonate, pale grayish yellow, Light Buff, Pale Olive-Buff, gray, Light Olive-Gray, olive-gray, Light Grayish-Olive, to grayish black, Deep Olive-Gray, Iron Gray.

Sporodochia 1–3 cells thick, highly irregular, initially consisting of small groups or chains of conidiogenous cells, in older cultures becoming irregular, confluent masses of greater than 50 conidiogenous cells. Conidiogenous cells proliferating enteroblastically, with conidia seceding at the same level, occurring singly, but more often aggregated, arising directly from pigmented superficial mycelium, globose, subglobose, or irregularly ellipsoidal, compressed when aggregated, smooth, 9.5–14.5 μm in diam., with necks 2.5–4 μm long, pale brown to blackish brown in KOH, usually darkest at the base of the neck, with a single cylindrical to widely flaring collarette, with collarettes 2–7.5 μm wide, often with collarettes forming a ragged fringe. Conidia, blastic, aseptate, with highly refractive cytoplasm, broadly falcate or lunate, narrowed at apex and base to form terminal appendages, 16.5–25×6.5–8.5 μm (including appendages), with appendages 1–3 μm, hyaline. Hyphae 1.5–4 μm in diam., septate, branched, hyaline to pale olive gray in KOH.

Although the invention is discussed principally with respect to the specific strains, it is well known in the an that the properties of microorganisms can be varied naturally and artificially. Thus, all strains of the genus Mycoleptodiscus, including varieties and mutants, whether obtained by selection from natural populations, produced by the action of mutating agents such as ionizing radiation or ultraviolet irradiation, or by the action of chemical mutagens such as nitrosoguanidine, are contemplated to be within the scope of this invention.

The production of the compound may be carried out by cultivating the fungus ATCC Designation 74336 or any strain of *Mycoleptodiscus atromaculans* in a suitable nutrient medium under conditions described herein until a substantial amount of antifungal activity is detected in the fermentation broth, harvesting by extracting the active components from the mycelial growth with a suitable solvent, concentrating the solution containing the desired component, then subjecting the concentrated material to chromatographic separation to isolate the compound from other metabolites also present in the cultivation medium.

Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium. Certain carbon sources are preferred as hereinafter set forth.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extract, corn steep liquors, distillers solubles, cottonseed meal, meat extract, and the like. The various sources of nitrogen can be used alone or in combination in amounts ranging from 0.05 to 5 percent by weight of the medium.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Representative suitable solid and liquid production media may be seen in the tables which follow. Also included are two representative seed media.

TABLE 1

| Seed Medium 1 | |
|---|---|
| Component | g/L |
| Yeast extract | 4.0 |
| Malt extract | 8.0 |
| Glucose | 4.0 |
| Junlon | 1.5 |

The medium was prepared with distilled water with the pH adjusted to 7.0 prior to sterilization. The medium was dispensed at 54 ml per 250 ml unbaffled Erlenmeyer flask. Cotton closures were used. Sterilization was at 121° C. for 20 minutes.

| Seed Medium 2 | | Trace Elements #2 | |
|---|---|---|---|
| Component | per liter | Component | per liter |
| Corn Steep Liquor | 5.0 gm | $FeSO_4.7H_2O$ | 1.0 gm |
| Tomato Paste | 40.0 gm | $MnSO_4.H_2O$ | 1.0 gm |
| Oat Flour | 10.0 gm | $CuCl_2.2H_2O$ | 0.025 gm |
| Glucose | 10.0 gm | $CaCl_2$ | 0.1 gm |
| Trace Elements #2 | 10 ml | $H_3BO_3$ | 0.056 gm |
| | | $(NH_4)_6MoO_2.4H_2O$ | 0.019 gm |
| Distilled water | to 1 liter | $ZnSO_4.7H_2O$ | 0.2 gm |
| | | Distilled water | to 1 liter |

The medium was prepared with distilled water with the pH adjusted to 6.8 prior to sterilization. The medium was dispensed at 50 ml per 250 ml unbaffled Erlenmeyer flask. Cotton closures were used. Sterilization was at 121° C. for 20 minutes.

TABLE 2

Production Medium 1

1. Solid portion:
Add 675 cc vermiculite to a 2-liter roller bottle. Plug with latex closure; autoclave for 60 min., plus 30 min. dry.

| 2. Liquid portion: | | K Elements | |
| --- | --- | --- | --- |
| Component | g/L | Component | g/L |
| Sucrose | 60.0 | $FeCl_3.6H_2O$ | 5.8 |
| Glucose | 80.0 | $MnSO_4.H_2O$ | 0.1 |
| Glycerol | 60.0 | $CoCl_2.6H_2O$ | 0.02 |
| Tomato paste | 5.0 | $CuSO_4.5H_2O$ | 0.015 |
| Ardamine pH | 5.0 | $NaMoO_4.2H_2O$ | 0.012 |
| $(NH4)_2SO_4$ | 2.0 | $ZnCl_2$ | 0.02 |
| $MgSO_4.7H_2O$ | 0.5 | $SnCl_2.2H_2O$ | 0.005 |
| $CaCl_2$ | 0.5 | $H_3BO_3$ | 0.01 |
| K-elements | 1 ml/L | KCl | 0.02 |
| | | HCl (concentrated) | 2.0 ml/L |

The medium was prepared with distilled water with the pH adjusted to 7.0 prior to sterilization. The medium was dispensed at 220 ml in 500 ml bottles. Sterilization was at 121° C. for 15 minutes.

| Production Medium 2 | |
| --- | --- |
| Component | per liter |
| Mannitol | 75.0 g. |
| Oat Flour | 15.0 g |
| Fidco Yeast Extract | 5.0 g |
| L-glutamic acid | 4.0 g |
| MES* | 16.2 g |
| Distilled water | to 1 liter |

*2[N-Morpholino]ethanesulfonic acid

The medium was prepared with distilled water with the pH adjusted to 6.0 with NaOH prior to sterilization. The medium was dispensed at 50 ml per 250 ml unbaffled Erlenmeyer flask. Cotton closures were used. Sterilization was at 121° C. for 20 minutes.

In the production of the compound, generally, the culture is first grown in a seed medium and the culture growth then used to inoculate a production medium. The production medium may be a solid medium or a liquid medium.

In carrying out the initial production of Compounds I and II, frozen vegetative mycelia of the culture were prepared from the fungal culture. The fungal culture was received on an agar slant and transferred aseptically to the seed medium. The flask was incubated on a 2-inch throw gyratory shaker, 220 rpm for 4 days at 25° C., 85% relative humidity to obtain biomass. Portions of the biomass were transferred into sterile vials containing glycerol and frozen at −75° C. A vial of the frozen vegetative mycelia was thawed to room temperature and used to inoculate seed cultures of the fungal culture at 1.0 ml/50 ml of seed medium. The culture was grown on a gyratory shaker at 220 rpm for 7 days at 25° C. and 85% relative humidity.

An aliquot (12 ml) of the grown seed was placed into 220 ml of the liquid portion of production medium 1. This was swirled vigorously to disperse the biomass. The contents were dispensed by pouring into a 2-liter roller culture vessel which contained 675 cubic centimeters of steam-sterilized large-particle vermiculite. The contents of the roller bottle were shaken/mixed to insure homogeneous inoculation and coverage. The roller bottles were incubated horizontally, revolving at approximately 4 rpm on a Wheaton roller apparatus, at 22° C., 75% relative humidity for 14 days, to obtain secondary metabolite production in the fermentation medium.

Subsequent fermentations for producing the compound used an improved liquid fermentation method as described below.

Media was prepared as described and dispensed, 50 ml of medium per 250 ml smooth bottom Erlenmeyer flask, and autoclaved for 20 minutes. Seed cultures were prepared by inoculating either of two seed media (Seed Medium 1 and Seed Medium 2) with 0.5 to 1.0 ml of a thawed frozen vegetative mycelia of the culture. In some cases the inoculum was an agar plug containing some culture growth cored out of an agar plate which had been streaked with the culture and incubated to form colonies. Seed flasks were incubated for 3–7 days to allow for the accumulation of biomass. Flasks containing production media 2 were inoculated with 2 ml of seed culture when the seed culture reached an appropriate cell density and incubated on a gyratory shaker (220 RPM) at 25° C. At selected time points (2 through 17 days) the production flasks were harvested. Fifty ml of methyl ethyl ketone (MEK) was added to each flask. The flasks were swirled and the contents poured into 100 ml bottles, capped and shaken for 1–1.5 hrs. 1 ml samples of the upper organic layer containing the compound were placed in glass test tubes, dried under nitrogen gas, and resuspended in methanol (0.1 ml to 0.5 ml). Samples were assayed for the compound by biological and HPLC assays.

Preferred media for the production of the compounds were found to be Seed Medium 2 with Production Medium 2 at 25° C.

The usefulness of the compounds as an antifungal agent, especially as an antimycotic agent, may be demonstrated with the compound in a broth microdilution assay for the determination of minimum inhibitory concentration (MIC) and minimum fungicidal concentration (MFC) against fungi. In such assay against a panel of fungi selected for their resistance/susceptibility to known compounds, animal virulence, source and clinical importance, the compounds were found to be effective at concentrations comparable to an established antifungal agent, amphotericin B.

In the microbroth dilution assay, the selected microorganisms were grown by streaking a yeast culture on Sabouraud Dextrose agar (SDA) and incubating for 24–48 hr at 35°–37° C. Thereafter, 3–5 characteristic colonies were selected and transferred to CM-YNB+0.1% Dextrose Agar plates (1% Bactopeptone, 0.5% yeast extract, 6.7 g/L yeast nitrogen base with amino acids, 1 µM adenine, 0.1% dextrose, and 1.5% Bacto agar) and incubated overnight at 35°–37° C. From the regrowth, 3 to 5 colonies were selected and suspended in 5 ml of CM-YNBD media (same as above, only without agar) and incubated for 4–6 hr at 35°–37° C. shaking at 225 rpm. The broth cultures were adjusted spectrophotometrically to 86% transmission resulting in a concentration of $1-5\times10^6$ cfu/ml which was further diluted 1:100 (1:50 for Aspergillus) in CM-YNBD to obtain a concentration of $1-5 \times10^4$ cfu/ml to use as inocula.

The test compounds were prepared as a stock solution of 512 µg/ml in 10% DMSO and 75 µl of said solution delivered to a well in column one of each 96 well, U-bottomed microtiter plate that already contained 75 µl of CM-YNBD media per well. In the first run of the assay, Compound I was then serially diluted two fold from column 1 to column 12 to yield concentrations from 256 µg/ml to 0.125 µg/ml.

Amphotericin B, the control compound, was prepared as a stock solution of 512 µg/ml in 10% DMSO and 75 µl of said solution delivered to a well in column one of each 96 well, U-bottomed microtiter plate that already contained 75 μl of CM-YNBD media per well. The compound was then serially diluted two fold from column 1 to column 12 to yield concentrations from 256 μg/ml to 0,125 μg/ml.

The plates containing the diluted compounds were then inoculated with 75 μl/well of the appropriate microorganism resulting in a further 2-fold dilution such that the final concentration of test compounds ranged between 128 and 0.06 μg/ml. The plates were incubated for 48 hours at 35°–37° C. with MIC (minimum inhibitory concentration) determinations carried out after 24 hours of incubation. Growth and sterility controls for each organism and sterility checks for the compounds also were carried out. In three cases, a modified MIC endpoint (MIC2) was used. MIC2 is defined as the lowest concentration that effects a prominent reduction in turbidity comparable to a drug-free control (Pfaller et al. Antimicrobial Agents and Chemotherapy, 34:1648–1654[90]).

After recording MICs at 24 hours, samples are withdrawn to determine the MFC. The microtiter plates were shaken gently to resuspend the cells and 1.5 μm sample was transferred from each well of the 96 well plate to the surface of a single reservoir inoculum plate containing 15 ml of SDA. The inoculated SDA and corresponding microtiter plates were incubated for 24 hours at 35°–37° C. For *Cryptococcus neoformans*, the MFC plates were inoculated after reading the 48 hour MICs and incubated for 48 hours before reading the MFC. The MFC is the lowest concentration of compound at which either no growth or growth of $\leq 3$ colonies occurs.

No MFC values are indicated for *Aspergillus fumigatus* since colony counts are unreliable with filamentous species. Instead, a Minimum Effective Concentration (MEC) is reported for *A. fumigatus*. The MEC is defined as the lowest concentration of drug which effects a severe morphological change in the cells. The MEC is scored macroscopically by direct observation of the microtiter plate wells after 24 hours and reflects microscopic alterations in cell morphology (Kurtz et al. AAC:38:1480–1489[94]).

The MIC, MIC2, MFC and MEC values for Compound I are shown in the following table:

| Strains | MIC | MFC | MEC |
|---|---|---|---|
| *Candida albicans* (MY1055) | 2* | <0.06 | |
| *Candida glabrata* (MY1381) | <0.06 | <0.06 | |
| *Candida parapsilosis* (MY1010) | <0.06 | <0.06 | |
| *Candida pseudotroplicalis* (MY2099) | <0.06 | <0.06 | |
| *Candida tropicalis* (MY1124) | 0.25* | 0.125 | |
| *Candida albicans* (CLY539) | 0.5* | >128 | |
| *Candida tropicalis* (MY1012) | 8 | 8 | |
| *Candida guillennondii* (MY1019) | >128 | >128 | |
| *Cryptococcus neoformans* (MY2062) | 32 | | |
| *Saccharomyces cerevisiae* (MY2140) | 8 | 4 | |
| *Saccharomyces cerevisiae* (MY2141) | <0.06 | <0.06 | |
| *Aspergillus fumigatus* (MF4839) | >128 | | 0.25 |
| *Aspergillus fumigatus* (MF5668) | >128 | | <0.06 |

*signifies use of an MIC2 definition: prominent decrease in turbidity. Other data represent complete clearing.

The following table shows comparative data for Compounds I and II and represents further testing with Compound I over that shown in the above table. In this run, Compound I was titrated from 64–0.03 μg/ml and Compound II was titrated from 128–0.06 μg/ml.

| Strains | I MIC | II MIC |
|---|---|---|
| *Candida albicans* (MY1055) | <0.03 | 1* |
| *Candida glabrata* (MY1381) | 4.03 | 0.5 |
| *Candida parapsilosis* (MY1010) | <0.03 | 2* |
| *Candida pseudotroplicalis* (MY2099) | <0.03 | <0.06 |
| *Candida tropicalis* (MY1124) | <0.03* | 0.5 |
| *Candida albicans* (CLY539) | <0.03* | >128* |
| *Candida tropicalis* (MY1012) | 8 | 8 |
| *Candida guillermondii* (MY1019) | >64 | >128 |
| *Cryptococcus neoformans* (MY2062) | >64 | >128 |
| *Saccharomyces cerevisiae* (MY2140) | 4 | 1 |
| *Saccharomyces cerevisiae* (MY2141) | <0.03 | <0.06 |
| *Aspergillus fumigatus* (MF4839) | >64 | >128 |
| *Aspergillus fumigatus* (MF5668) | >64 | >128 |
| *Candida albicans* (CA2) | >64 | >128 |

*signifies use of an MIC2 definition: prominent decrease in turbidity. Other data represents complete clearing.

Compounds I and II are also useful for inhibiting the growth of filamentous fungi. Such use may be illustrated in the following tests with *Aspergillus flavus, Fusarium oxysporum, Ustilago zeae* and the like.

Inocula for filamentous fungi are prepared by scraping the surface of stock plates maintained on potato dextrose agar with a moistened sterile dacron swab. The spores and mycelia are then suspended in 10 mL of sterile potato dextrose broth and adjusted to 70% percent transmission at 660 nm.

The samples to be tested for production of antifungal agent are applied directly to the agar plates as methanol solutions. When the sample to be tested is crude broth, it may be centrifuged prior to application. The assay plates are then incubated at either 28° C. or 37° C. for 24 hours. Following incubation, the inhibition zones are measured. Growths are also noted as to appearance. The compounds are seen to effectively inhibit growth of the fungal organisms.

The following examples illustrate the invention but are not to be construed as limiting the invention disclosed herein.

EXAMPLE 1

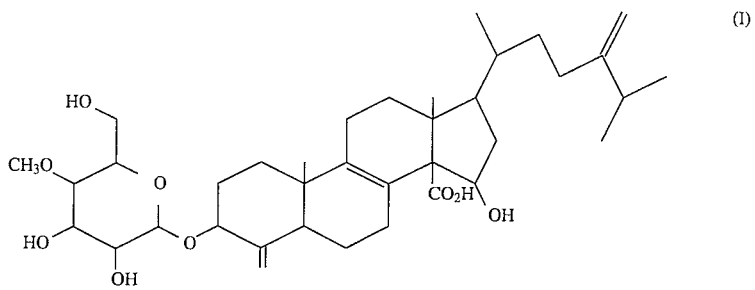

(I)

Isolation of Compound I

A methyl ethyl ketone (MEK) extract of a batch fermentation of culture MF 5928 (ATCC Designation 74336) corresponding to 1500 mL of whole broth was concentrated in vacuo to 75 mL. The concentrate was extracted twice with an equal volume of ethyl acetate. The ethyl acetate layer was dried over anhydrous $Na_2SO_4$ and concentrated to an oil. This oil was dissolved in 50 mL of methanol and extracted twice with an equal volume of hexanes solvent. The methanol layer was concentrated in vacuo to approximately 1 mL of oil. The oil was dissolved in 5 parts methanol in 95 parts methylene chloride to a final volume of 5 mL. A 4.8 mL portion (812 mg syrup) was applied to a 150 mL silica gel 60 (0.040–0.0630 mm, 230–400 mesh, E. Merck) flash chromatograghy column equilibrated with 5% methanol in methylene chloride. The column was eluted by a step gradient of 450 mL each of 5, 10, 20, and 30% methanol in methylene chloride followed by 450 mL of methanol. Thirty fifteen mL fractions were collected from each solvent system. The product rich fractions 71–110 were determined by biological assay.

The crude fraction pool was concentrated in vacuo to 154 mg of an oil and dissolved in methanol. This sample was further purified in two identical HPLC separations (Zorbax Rx-C8, 7 mm, 21.2 mm×250 mm, eluted with mobile phase consisting of 75% methanol/25% aqueous 0.01 M $K_2HPO_4$ adjusted to pH 6.9 with concentrated $H_3PO_4$, flow rate 20 mL/min. at room temperature, diode array detection). Ten mL fractions were collected. The product rich fractions 49–58 and 53–65 were pooled separately and concentrated in vacuo to approximately 25% of their orginal volumes. Each was extracted with an equal volume of ethyl acetate and the combined ethyl acetate layers were washed with an equal volume of brine, dried over anhydrous $Na_2SO_4$ and concentrated in vacuo to yield 21 mg of Compound I.

EXAMPLE 2

Isolation of Compound I

A MEK extract of a batch fermentation of culture MF 5928 corresponding to 1674 mL of whole broth was concentrated in vacuo to an oily aqueous layer. The concentrate was diluted with water and extracted with an equal volume of heptane. The aqueous layer was extracted with an equal volume of ethyl acetate. The ethyl acetate layer was rinsed with an equal volume of water followed by an equal volume of brine and was dried over anhydrous $Na_2SO_4$. The ethyl acetate layer was concentrated to dryness in vacuo and weighed 441 mg. The residue was dissolved in 5 parts methanol in 95 parts methylene chloride to a final volume of approximately 5 mL. A 428 mg portion was applied to a 100 mL silica gel 60 (0.040–0.0630 mm, 230–400 mesh, E. Merck) column equilibrated with 5% methanol in methylene chloride containing 1% water. The column was eluted by a step gradient of 300 mL each of 5 and 10% methanol in methylene chloride followed by 500 mL of 20% and 200 mL of 30% methanol (all solvents contained 1% water). The elution flow rate was approximately 7 mL/minute and ten mL fractions were collected. Fractions 59–64 contained Compound I as determined by TLC and HPLC comparison to an authentic sample, and were pooled. The TLC conditions for Compound I were as follows: Silica gel 60 F-254 E. Merck, developed with methylene chloride/methanol (8:2) containing 1% water, visualized by spraying with a solution of 0.5% panisaldehyde and 10% $H_2SO_4$ in 50% EtOH followed by heating, $R_f$=0.59. The HPLC conditions for Compound I were as follows: Zorbax Rx-C8 5 mm, 4.6 mm×250 mm, eluted with mobile phase consisting of 65% methanol/35% aqueous 0.01 M $K_2HPO_4$ adjusted to pH 6.9 with concentrated $H_3PO_4$, flow rate 1 mL/min. at 40° C., diode array detection, $t_R$=11.7 minutes.

The crude fraction pool was concentrated in vacuo to 32 mg. A 24 mg portion was further purified by high speed countercurrent chromatography (using a Countercurrent Chromatograph obtained from P.C., Inc., Potomac, Md.). The feed was dissolved in a small amount of the lower phase of a solvent system consisting of 5 parts hexanes/3 parts methanol/2 parts aqueous 0.01 M $K_2HPO_4$ pH 6.9. The sample was applied to the head of a #14 Tripple coil (240 mL, P.C., Inc.) which had been filled completely with the upper phase of the above solvent system. The coil was then eluted with the lower phase of the solvent system at 3 mL/min from the head to the tail of the column, at a rotation speed of 800 rpm in the forward direction collecting 3.0 mL fractions. The product rich fractions 50–77 were determined by TLC, as described above, and were concentrated to dryness in vacuo. The residue was dissolved in 64 mL of ethyl acetate and partitioned between the ethyl acetate and an equal volume of aqueous 0.1% $H_3PO_4$ adjusted to pH 3. The ethyl acetate layer was washed with equal volumes of water and brine solution and dried over $Na_2SO_4$. It was concentrated to dryness in vacuo and 19 mg of Compound I was obtained.

Compound I had the spectral properties previously described.

EXAMPLE 3

Isolation of Compound II

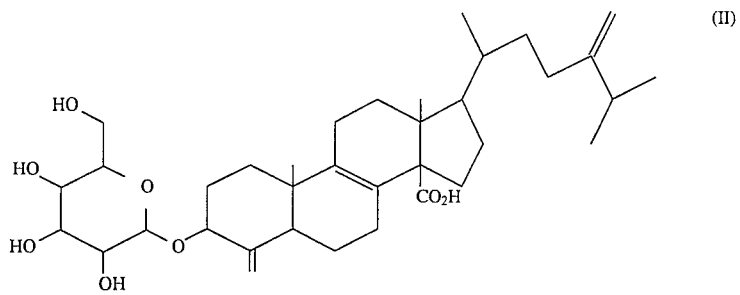
(II)

A methyl ethyl ketone (MEK) extract of a batch fermentation of culture MF 5928 corresponding to 2830 mL of whole broth was concentrated in vacuo to an oily aqueous layer. This concentrate was diluted with water and extracted with an equal volume of heptane. The heptane layer was re-extracted with methanol and the aqueous layer was extracted twice with an equal volume of ethyl acetate. The original aqueous layer from the MEK extraction was re-extracted with an equal volume of ethyl acetate. The methanol and three ethyl acetate layers were combined for concentration to dryness in vacuo. The residue, weighing 8.0 g, was dissolved in 5 parts methanol in 95 parts methylene chloride to a final volume of 200 mL. A 7.98 g portion was applied to a 2 L silica gel 60 (0.040–0.0630 mm, 230–400 mesh, E. Merck) column equilibrated with 5% methanol in methylene chloride containing 1% water. The column was eluted by a step gradient of 3.75 L of 5% methanol in methylene chloride followed by 10 L each of 10% and 20% and completed with 3.25 L of 30% methanol (all solvents contained 1% water). The elution flow rate was approximately 200 mL/minute and 250 mL fractions were collected. The product rich fractions 30–37 contained Compound I ($R_f$=0.59) and 38–50 contained Compound II ($R_f$=0.44) as determined by the TLC system cited in Example 2.

The crude fraction pool was concentrated in vacuo to 600 mg. The oil was dissolved in 5 mL of 9 parts hexanes-ethyl acetate (1:1) and 1 part methanol solution containing 1% water overall and was applied to a 100 mL silica gel 60 (0.040–0.0630 mm, 230–400 mesh, E. Merck) column equilibrated with the feed solvent. The elution was isocratic at a flow rate of approximately 3 mL/minute and one minute fractions were collected. The product rich fractions 63–82 were determined by TLC, as described above, and were concentrated to dryness in vacuo weighing 113.5 mg. This residue was dissolved in 2 mL of 1 part methanol in 9 parts methylene chloride and loaded on a 28 mL silica gel 60 (0.040–0.0630 mm, 230–400 mesh, E. Merck) column equilibrated with the same solvent. The elution was isocratic at a flow rate of approximately 1.2 mL/minute and 2.5 minute fractions were collected. The product rich fractions 56–128 containing Compound II were determined by the TLC system described above. This pool was concentrated to dryness in vacuo and 16.8 mg of Compound II was obtained.

Compound II had the spectral properties previously described.

The following examples illustrate representative compositions containing Compounds I or II.

EXAMPLE A 1000 compressed tablets each containing 500 mg of Compound I are prepared from the following formulation:

|  | grams |
| --- | --- |
| Compound I | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE B

|  | grams |
| --- | --- |
| Compound I | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE C 250 mL of an injectible solution are prepared by conventional procedures from the following formulation:

| Dextrose | 12.5 g |
| --- | --- |
| Water | 250 mL |
| Compound I | 400 mg |

The ingredients are blended and thereafter sterilized for use.

EXAMPLE D

An ointment suitable for topical application may be prepared by intimately dispersing 13 mg of Compound I in 1 g of commercially available polyethylene/hydrocarbon gel.

EXAMPLE E

An aerosol composition may be prepared having the following formulation (per canister):

| | |
|---|---|
| Compound I | 24 mg |
| Lecithin NF, liquid concentrate | 1.2 mg |
| Trichlorofluoromethane | 4.025 g |
| Dichlorodefluoromethane | 12.15 g |

What is claimed is:

1. A compound having the structure:

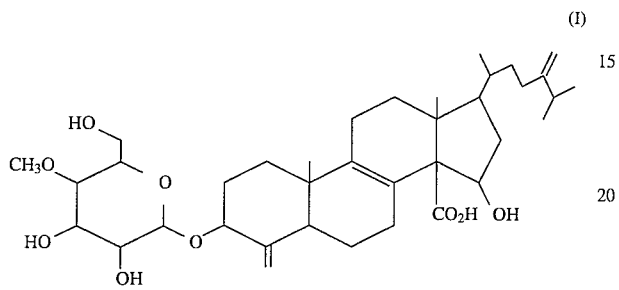

(I)

2. An antifungal composition comprising an antifungally effective amount of the compound of claim 1 and a pharmaceutically acceptable carrier therefor.

3. A method for combatting fungal infections in mammals which comprises administering to a region of the animal afflicted with said fungi a therapeutically effective amount of the compound of claim 1.

4. A compound having the structure:

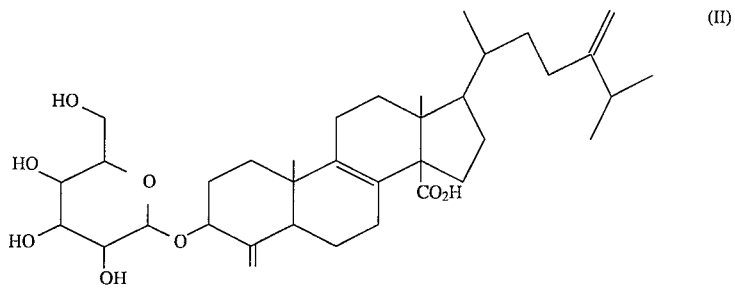

(II)

5. An antifungal composition comprising an antifungally effective amount of the compound of claim 4 and a pharmaceutically acceptable carrier therefor.

6. A method for combatting fungal infections in mammals which comprises administering to a region of the animal afflicted with said fungi a therapeutically effective amount of the compound of claim 4.

7. An antifungal composition comprising an antifungally effective amount of a combination of compounds I and II of the structure

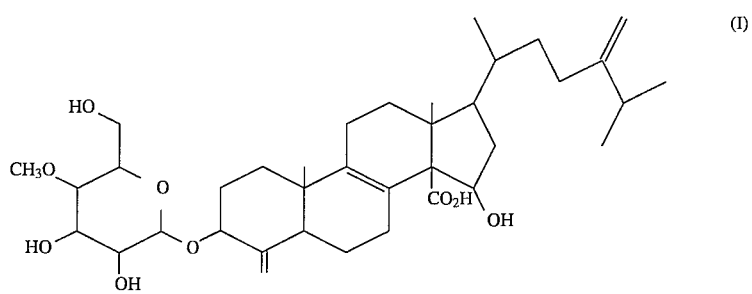

(I)

and

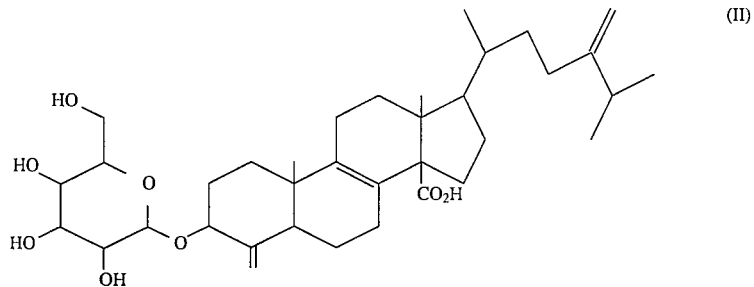
(II)
and a pharmaceutically acceptable carrier therefor.
* * * * *